(12) United States Patent
Haefner

(10) Patent No.: US 7,865,233 B2
(45) Date of Patent: Jan. 4, 2011

(54) SUBCUTANEOUS CARDIAC SIGNAL DISCRIMINATION EMPLOYING NON-ELECTROPHYSIOLOGIC SIGNAL

(75) Inventor: Paul Haefner, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 761 days.

(21) Appl. No.: 10/784,478

(22) Filed: Feb. 23, 2004

(65) Prior Publication Data

US 2005/0119708 A1    Jun. 2, 2005

Related U.S. Application Data

(60) Provisional application No. 60/462,272, filed on Apr. 11, 2003.

(51) Int. Cl.
*A61B 5/0452* (2006.01)
(52) U.S. Cl. .................................................... 600/513
(58) Field of Classification Search ............ 600/509, 600/513, 514, 515, 301, 528, 510, 508; 128/923, 128/924, 901
See application file for complete search history.

(56) References Cited

U.S. PATENT DOCUMENTS

| | | | |
|---|---|---|---|
| RE30,750 E | * | 9/1981 | Diack et al. .................... 607/5 |
| 4,562,841 A | | 1/1986 | Brockway et al. |
| 4,674,518 A | | 6/1987 | Salo |
| 4,784,162 A | | 11/1988 | Ricks et al. |
| 4,827,943 A | | 5/1989 | Bornn et al. |
| 4,953,551 A | | 9/1990 | Mehra et al. |
| 5,036,849 A | | 8/1991 | Hauck et al. |
| 5,058,583 A | | 10/1991 | Geddes |
| 5,113,869 A | * | 5/1992 | Nappholz et al. ........... 600/508 |
| 5,117,824 A | | 6/1992 | Keimel |
| 5,133,353 A | | 7/1992 | Hauser |
| 5,170,784 A | | 12/1992 | Ramon et al. |
| 5,176,137 A | | 1/1993 | Erickson |
| 5,179,945 A | | 1/1993 | Van Hofwegen et al. |
| 5,203,348 A | | 4/1993 | Dahl et al. |
| 5,209,229 A | | 5/1993 | Gilli |

(Continued)

FOREIGN PATENT DOCUMENTS

EP    0488512    6/1992

(Continued)

OTHER PUBLICATIONS

Renee Hartz et al., *New Approach to Defibrillator Insertion*, J. Thoracic Cardiovascular Surgery, vol. 97, pp. 920-922 (1989).

(Continued)

*Primary Examiner*—Michael Kahelin
(74) *Attorney, Agent, or Firm*—Hollingsworth & Funk, LLC

(57) ABSTRACT

A cardiac monitoring and/or stimulation system includes a housing coupled to a plurality of electrodes configured for subcutaneous non-intrathoracic sensing. A signal processor receives a plurality of composite signals associated with a plurality of sources, separates a signal from the plurality of composite signals, and identifies the separated signal as a cardiac signal using information derived from a non-electrophysiologic sensor, such as an accelerometer or acoustic transducer. The signal processor may iteratively correlate separated signals from the plurality of composite signals with a non-electrophysiologic sensor signal until the cardiac signal is identified.

26 Claims, 12 Drawing Sheets

U.S. PATENT DOCUMENTS

| | | |
|---|---|---|
| 5,230,337 A | 7/1993 | Dahl et al. |
| 5,261,400 A | 11/1993 | Bardy |
| 5,284,136 A | 2/1994 | Hauck et al. |
| 5,292,338 A | 3/1994 | Bardy |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck et al. |
| 5,330,505 A | 7/1994 | Cohen |
| 5,331,966 A | 7/1994 | Bennett et al. |
| 5,334,222 A | 8/1994 | Salo et al. |
| 5,342,404 A | 8/1994 | Alt et al. |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,388,578 A * | 2/1995 | Yomtov et al. ............... 600/375 |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,539 A | 5/1995 | Neisz |
| 5,417,714 A | 5/1995 | Levine et al. |
| 5,439,482 A | 8/1995 | Adams et al. |
| 5,441,518 A | 8/1995 | Adams et al. |
| 5,449,652 A | 9/1995 | Swartz |
| 5,464,434 A | 11/1995 | Alt |
| 5,468,254 A | 11/1995 | Hahn et al. |
| 5,531,779 A | 7/1996 | Dahl et al. |
| 5,540,727 A | 7/1996 | Tockman et al. |
| 5,545,186 A | 8/1996 | Olson et al. |
| 5,545,202 A | 8/1996 | Dahl et al. |
| 5,556,421 A | 9/1996 | Prutchi et al. |
| 5,601,611 A | 2/1997 | Fayram |
| 5,603,732 A | 2/1997 | Dahl et al. |
| 5,606,969 A | 3/1997 | Butler et al. |
| 5,620,466 A | 4/1997 | Haefner et al. |
| 5,634,938 A | 6/1997 | Swanson et al. |
| 5,641,326 A | 6/1997 | Adams |
| 5,662,688 A | 9/1997 | Haefner et al. |
| 5,687,738 A * | 11/1997 | Shapiro et al. ............... 600/528 |
| 5,697,953 A | 12/1997 | Kroll et al. |
| 5,704,365 A | 1/1998 | Albrecht et al. |
| 5,724,984 A | 3/1998 | Arnold et al. |
| 5,827,326 A | 10/1998 | Kroll et al. |
| 5,836,987 A | 11/1998 | Baumann et al. |
| 5,855,593 A | 1/1999 | Olson et al. |
| 5,895,414 A | 4/1999 | Sanchez-Zambrano |
| 5,916,243 A | 6/1999 | KenKnight et al. |
| 5,919,141 A | 7/1999 | Money et al. |
| 5,957,956 A | 9/1999 | Kroll et al. |
| 5,961,446 A | 10/1999 | Beller et al. |
| 5,961,450 A | 10/1999 | Merchant et al. |
| 6,026,320 A | 2/2000 | Carlson et al. |
| 6,044,298 A | 3/2000 | Salo et al. |
| 6,050,940 A | 4/2000 | Braun et al. |
| 6,055,454 A | 4/2000 | Heemels |
| 6,115,628 A | 9/2000 | Stadler et al. |
| 6,122,536 A | 9/2000 | Sun et al. |
| 6,141,581 A | 10/2000 | Olson et al. |
| 6,144,879 A | 11/2000 | Gray |
| 6,148,230 A | 11/2000 | KenKnight |
| 6,198,952 B1 | 3/2001 | Miesel |
| 6,208,888 B1 | 3/2001 | Yonce |
| 6,221,011 B1 | 4/2001 | Bardy |
| 6,227,072 B1 | 5/2001 | Ritchey et al. |
| 6,259,947 B1 | 7/2001 | Olson et al. |
| 6,270,457 B1 | 8/2001 | Bardy |
| 6,277,072 B1 | 8/2001 | Bardy |
| 6,280,380 B1 | 8/2001 | Bardy |
| 6,280,462 B1 | 8/2001 | Hauser et al. |
| 6,285,907 B1 | 9/2001 | Kramer et al. |
| 6,312,378 B1 | 11/2001 | Bardy |
| 6,336,903 B1 | 1/2002 | Bardy |
| 6,358,203 B2 | 3/2002 | Bardy |
| 6,368,284 B1 | 4/2002 | Bardy |
| 6,371,922 B1 | 4/2002 | Baumann et al. |
| 6,375,614 B1 | 4/2002 | Braun et al. |
| 6,398,728 B1 | 6/2002 | Bardy |
| 6,409,675 B1 | 6/2002 | Turcott |
| 6,411,848 B2 | 6/2002 | Kramer et al. |
| 6,415,174 B1 | 7/2002 | Bebehani et al. |
| 6,424,865 B1 | 7/2002 | Ding |
| 6,438,406 B2 | 8/2002 | Yonce |
| 6,438,410 B2 | 8/2002 | Hsu et al. |
| 6,440,066 B1 | 8/2002 | Bardy |
| 6,440,082 B1 | 8/2002 | Joo |
| 6,454,708 B1 | 9/2002 | Ferguson et al. |
| 6,459,929 B1 | 10/2002 | Hopper et al. |
| 6,477,406 B1 | 11/2002 | Turcott |
| 6,480,733 B1 | 11/2002 | Turcott |
| 6,487,443 B2 | 11/2002 | Olson et al. |
| 6,491,639 B1 | 12/2002 | Turcott |
| 6,496,715 B1 | 12/2002 | Lee et al. |
| 6,496,721 B1 | 12/2002 | Yonce |
| 6,505,067 B1 | 1/2003 | Lee et al. |
| 6,512,940 B1 | 1/2003 | Brabec et al. |
| 6,522,915 B1 | 2/2003 | Ceballos et al. |
| 6,542,775 B2 | 4/2003 | Ding et al. |
| 6,564,106 B2 | 5/2003 | Guck et al. |
| 6,597,951 B2 | 7/2003 | Krammer et al. |
| 6,607,509 B2 | 8/2003 | Bobroff et al. |
| 6,615,083 B2 | 9/2003 | Kupper |
| 6,622,046 B2 | 9/2003 | Fraley et al. |
| 6,628,986 B1 | 9/2003 | Mouchawar et al. |
| 6,643,540 B2 | 11/2003 | Yonce |
| 6,650,940 B1 | 11/2003 | Zhu et al. |
| 6,684,101 B2 | 1/2004 | Daum |
| 6,701,170 B2 | 3/2004 | Stetson |
| 6,925,325 B2 | 8/2005 | Yonce |
| 6,950,694 B2 | 9/2005 | Yonce |
| 7,218,966 B2 | 5/2007 | Haefner |
| 7,302,294 B2 | 11/2007 | Kamath et al. |
| 7,715,916 B2 | 5/2010 | Haefner |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082658 A1 | 6/2002 | Heinrich et al. |
| 2002/0085741 A1 | 7/2002 | Shimizu |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107552 A1 | 8/2002 | Gilkerson et al. |
| 2002/0107559 A1 | 8/2002 | Sanders et al. |
| 2002/0120299 A1 | 8/2002 | Ostroff et al. |

| | | | |
|---|---|---|---|
| 2002/0136328 | A1 | 9/2002 | Shimizu |
| 2002/0147474 | A1 | 10/2002 | Morris et al. |
| 2003/0004546 | A1 | 1/2003 | Casey |
| 2003/0004552 | A1 | 1/2003 | Plombon et al. |
| 2003/0023175 | A1 | 1/2003 | Arzbaecher et al. |
| 2003/0036778 | A1 | 2/2003 | Ostroff et al. |
| 2003/0045904 | A1 | 3/2003 | Bardy et al. |
| 2003/0060723 | A1 | 3/2003 | Joo et al. |
| 2003/0069609 | A1 | 4/2003 | Thompson |
| 2003/0088278 | A1 | 5/2003 | Bardy et al. |
| 2003/0088279 | A1 | 5/2003 | Rissmann et al. |
| 2003/0088280 | A1 | 5/2003 | Ostroff |
| 2003/0088281 | A1 | 5/2003 | Ostroff et al. |
| 2003/0088282 | A1 | 5/2003 | Ostroff |
| 2003/0088283 | A1 | 5/2003 | Ostroff |
| 2003/0088286 | A1 | 5/2003 | Ostroff et al. |
| 2003/0097153 | A1 | 5/2003 | Bardy et al. |
| 2003/0204146 | A1 | 10/2003 | Carlson |
| 2003/0212436 | A1 | 11/2003 | Brown |
| 2004/0111021 | A1 | 6/2004 | Olson |
| 2004/0172066 | A1 | 9/2004 | Wagner et al. |
| 2004/0220633 | A1 | 11/2004 | Wagner et al. |
| 2004/0230230 | A1 | 11/2004 | Lindstrom |
| 2004/0260522 | A1 | 12/2004 | Albera |
| 2005/0010120 | A1 | 1/2005 | Jung |
| 2005/0119708 | A1 | 6/2005 | Haefner |
| 2005/0240234 | A1* | 10/2005 | Joo et al. ................. 607/6 |

FOREIGN PATENT DOCUMENTS

| | | |
|---|---|---|
| WO | WO9217240 | 10/1992 |
| WO | WO 92/20402 | 11/1992 |
| WO | WO03003905 | 1/2003 |
| WO | WO03020367 | 3/2003 |

OTHER PUBLICATIONS

Theofilos M. Kolettis, MD, PhD et al., *Submammary Implantation of a Cardioverter-Defibrillator with a Nonthoractomy Lead System*, Am. Heart J., vol. 126, pp. 1222-1223 (Nov. 1993).

John C. Schuder et al., *Transthoracic Ventricular Defibrillation in the Dog with Truncated and Untruncated Exponential Stimuli*, IEEE Trans. On Bio-Medical Engin., vol. BME-18, No. 6, pp. 410-415 (Nov. 1971).

John C. Schuder et al., *Ventricular Defibrillation in the Dog Using Implanted and Partially Implanted Electrode Systems*, Am. J. of Cardiology, vol. 33, pp. 243-247 (Feb. 1974).

John C. Schuder et al., *Experimental Ventricular Defibrillation with an Automatic and Completely Implanted System*, Trans. Am. Soc. Artif. Int. Organs, vol. 16, pp. 207-212 (1970).

Karel Smits & Marek Malik, *Defibrillation Threshold (DFT) Model of a Fully Subcutaneous ICD System*, Europace Supplements, vol. 2, Jun. 2001 at col. 778, p. B83.

Stirbis et al., *Optmizing the Shape of Implanted Artificial Pacemakers*, Kaunas Medical Institute. Translated from Meditsinskaya Tekhnika, No. 6, pp. 25-27 (1986).

Charles T. Leng et al., *Lead Configuration for Defibrillator Implantation in a Patient with Congenital Heart Disease and a Mechanical Prosthetic Tricuspid Valve*, PACE, vol. 24, No. 8, pp. 1291-1292 (Aug. 2001).

Park & Pollock, *Use of an Implantable Cardioverter Defibrillator in an Eight-Month-Old Infant with Ventricular Fibrillation Arising from a Myocardial Fibroma*, PACE, vol. 22, No. 1, pp. 138-139 (Jan. 1999).

Rainer Gradaus M.D. et al., *Nonthoracotomy Implantable Cardioverter Defibrillator Placement in Children: Use of a Subcutaneous Array Leads and Abdominally Placed Implantable Cardioverter Defibrillators in Children*, J. Of Cardiovascular Electrophysiology, vol. 12, No. 3, pp. 356-360 (Mar. 2001).

Belouchrani et al., Blind Source Separation Based on Time-Frequency Signal Representations, IEEE Transactions on Signal Processing, vol. 46, No. 11, pp. 2888-2897, Nov. 1998.

Comon, Independent component analysis, A new concept?, Signal Processing, vol. 36, No. 3, pp. 287-314, Apr. 1994.

Gallois et al., Multi-Channel Analysis of the EEG Signals and Statistic Particularities for Epileptic Seizure Forecast, Second Joint EMBS/BMES Conference, pp. 208-215, Oct. 23-26, 2002.

Hyvärinen et al., Independent Component Analysis: A Tutorial, Helsinski Univ. of Technology, Apr. 1999.

Krahn et al., Recurrent syncope. Experience with an implantable loop record. Cardiol. Clin., vol. 15(2), May 1997, pp. 316-326.

Rieta, et al., Atrial Activity Extraction Based on Blind Source Separation as an Alternative to QRST Cancellation for Atrial Fibrillation Analysis, Computers in Cardiology, vol. 27, pp. 69-72, 2000.

Smits et al., Defibrillation Threshold (DFT) Model of a Fully Subcutaneous ICD System, Europace Supplements, vol. 2, Jun. 2001 at col. 778, p. B83.

Zarzoso et al., Blind Separation of Independent Sources for Virtually Any Source Probability Density Function, IEEE Transactions on Signal Processing, vol. 47, No. 9, pp. 2419-2432, Sep. 1999.

Zarzoso et al., Noninvasive Fetal Electrocardiogram Extraction: Blind Separation Versus Adaptive Noise Cancellation, IEEE Transactions on Biomedical Engineering, vol. 48, No. 1, pp. 12-18, Jan. 2001.

Office Action dated Aug. 7, 2006 from U.S. Appl. No. 10/804,471, 15 pages.

Office Action Response submitted Nov. 7, 2006 to office action dated Aug. 7, 2006 from U.S. Appl. No. 10/804,471, 14 pages.

Notice of Alowance dated Jan. 3, 2007 from U.S. Appl. No. 10/804,471, 7 pages.

Office Action dated Aug. 27, 2009 from U.S. Appl. No. 11/803,548, 9 pages.

Office Action Response submitted Oct. 20, 2009 to office action dated Aug. 27, 2009 from U.S. Appl. No. 11/803,548, 10 pages.

Notice of Allowance dated Dec. 11, 2009 from U.S. Appl. No. 11/803,548, 7 pages.

Office Action dated May 9, 2006 from U.S. Appl. No. 10/817,749, 23 pages.

Office Action Response submitted Oct. 10, 2006 to office action dated May 9, 2006 from U.S. Appl. No. 10/817,749, 22 pages.

Office Action dated Mar. 20, 2007 from U.S. Appl. No. 10/817,749, 23 pages.

Office Action Response submitted May 21, 2007 to office action dated Mar. 20, 2007 from U.S. Appl. No. 10/817,749, 16 pages.

Notice of Allowance dated Jul. 12, 2007 from U.S. Appl. No. 10/817,749, 8 pages.

Restriction dated Mar. 10, 2010 from U.S. Appl. No. 11/975,040, 6 pages.

Restriction Response submitted May 10, 2010 to restriction dated Mar. 10, 2010, 6 pages.

International Search Report from International application No. PCT/US2004/010917 dated Nov. 23, 2004, 12 pages.

International Preliminary Report on Patentablilty from International application No. PCT/US2004/010917 dated Oct. 27, 2005, 13 pages.

Office Action dated Mar. 31, 2009 from JP2006-509836, 6 pages.

Office Action response submitted Sep. 16, 2009 from JP2006-509836, 13 pages.

Notice of Allowance dated May 11, 2010 from JP2006-509836, 2 pages.

Office Action Response submitted Oct. 26, 2010 to office action dated Aug. 4, 2010 from U.S. Appl. No. 11/975,040, 10 pages.

* cited by examiner

SUBCUTANEOUS CARDIAC SIGNAL DISCRIMINATION EMPLOYING NON-ELECTROPHYSIOLOGIC SIGNAL

RELATED APPLICATIONS

This application claims the benefit of Provisional Patent Application Ser. No. 60/462,272, filed on Apr. 11, 2003, to which priority is claimed pursuant to 35 U.S.C. §119(e) and which is hereby incorporated herein by reference.

FIELD OF THE INVENTION

The present invention relates generally to implantable medical devices and, more particularly, to subcutaneous cardiac sensing and/or stimulation devices employing cardiac signal separation.

BACKGROUND OF THE INVENTION

The healthy heart produces regular, synchronized contractions. Rhythmic contractions of the heart are normally controlled by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and can be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia can quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Typical Implantable cardioverter/defibrillators (ICDs) include one or more endocardial leads to which at least one defibrillation electrode is connected. Such ICDs are capable of delivering high-energy shocks to the heart, interrupting the ventricular tachyarrhythmia or ventricular fibrillation, and allowing the heart to resume normal sinus rhythm. ICDs may also include pacing functionality.

Although ICDs are very effective at preventing Sudden Cardiac Death (SCD), most people at risk of SCD are not provided with implantable defibrillators. Primary reasons for this unfortunate reality include the limited number of physicians qualified to perform transvenous lead/electrode implantation, a limited number of surgical facilities adequately equipped to accommodate such cardiac procedures, and a limited number of the at-risk patient population that may safely undergo the required endocardial or epicardial lead/electrode implant procedure.

SUMMARY OF THE INVENTION

The present invention is directed to cardiac monitoring and/or stimulation methods and systems that, in general, provide transthoracic monitoring, defibrillation therapies, pacing therapies, or a combination of these capabilities. Embodiments of the present invention are directed to subcutaneous cardiac monitoring and/or stimulation methods and systems that detect and/or treat cardiac activity or arrhythmias.

According to one embodiment of the invention, a medical system includes a housing having a medical device disposed within the housing. The housing is coupled to a plurality of electrodes configured for subcutaneous non-intrathoracic sensing. A signal processor is coupled to the plurality of electrodes and configured to receive a plurality of composite signals associated with a plurality of sources sensed by at least some of the electrodes. The signal processor is further configured to separate a signal from the plurality of composite signals and identify the separated signal as a cardiac signal.

In another embodiment of the present invention, a system includes a housing coupled to a plurality of electrodes configured for subcutaneous non-intrathoracic sensing. A signal processor receives a plurality of composite signals associated with a plurality of sources, separates a signal from the plurality of composite signals using blind source separation, and identifies a cardiac signal using information from a non-electrophysiological cardiac source, such as from an accelerometer, acoustic transducer or other sensor that senses cardiac activity other than cardiac electrophysiology signals. The signal processor may iteratively correlate separated signals from the plurality of composite signals with the non-electrophysiological cardiac source signal until the cardiac signal is identified.

An embodiment of a method of signal separation involves detecting a plurality of composite signals at a plurality of locations, separating a signal using blind source separation, and identifying a cardiac signal using both electrical and non-electrical cardiac information. The method may also involve providing a detection window defined by a start time and a stop time determined using the non-electrophysiological cardiac source information. The QRS complex may be detected within the detection window.

The method may involve using acoustic emission information such as a temporal location of a peak heart-sound. The detection window may be defined by a start time preceding the temporal location of a peak heart-sound. The method may involve the use of other non-electrophysiological cardiac source information such as blood-flow information, pulse pressure information, and/or pulse oximetry information such as the pulse oximetry information generated using photoplethysmography. The method may also involve identifying the separated signal as the cardiac signal by providing a detection window within which the cardiac signal is correlated to the non-electrophysiological cardiac source.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
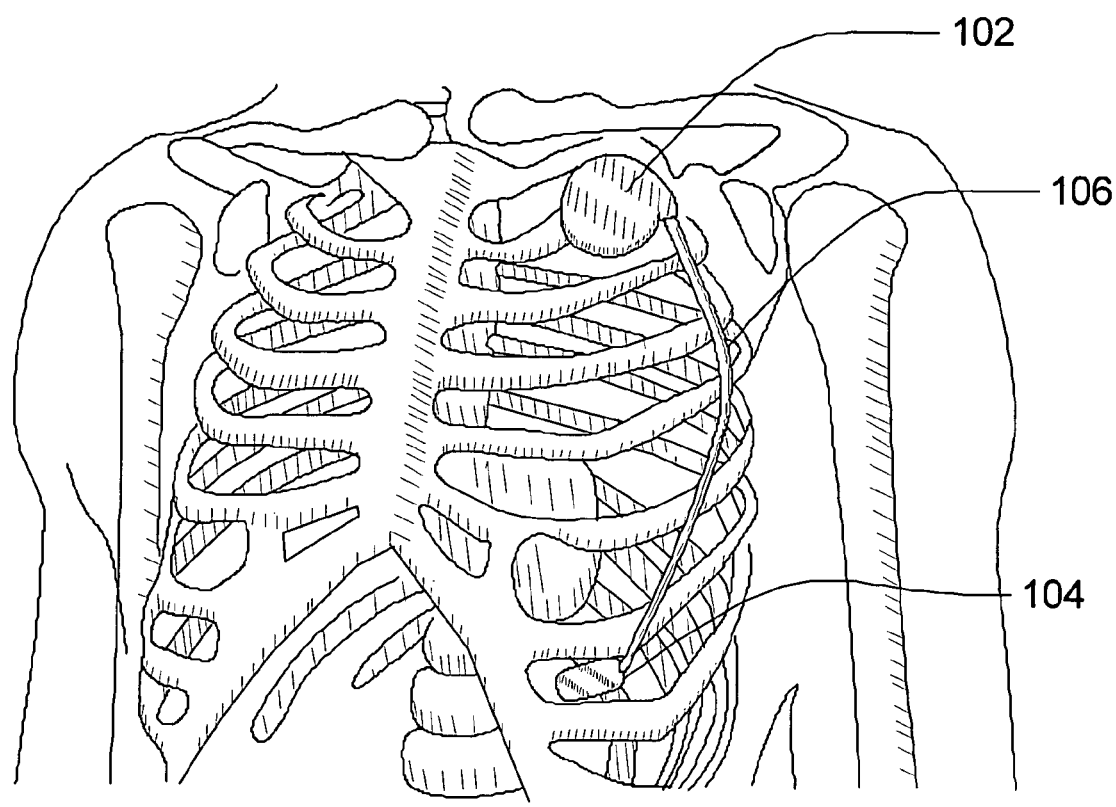
FIGS. 1A and 1B are views of a transthoracic cardiac sensing and/or stimulation device as implanted in a patient in accordance with an embodiment of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a cardiac monitor or a cardiac stimulator may be implemented to include one or more of the advantageous features and/or processes described below. It is intended that such a monitor, stimulator, or other implanted or partially implanted device need not include all of the features described herein, but may be implemented to include selected features that provide for unique structures and/or functionality. Such a device may be implemented to provide a variety of therapeutic or diagnostic functions.

In general terms, a cardiac signal detection arrangement and method may be used with a subcutaneous cardiac monitoring and/or stimulation device. One such device is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more leads incorporating electrodes may be located in direct contact with the heart, great vessel or coronary vasculature, such as via one or more leads implanted by use of conventional transvenous delivery approaches. In a further implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart. Examples of useful subcutaneous electrodes, electrode arrays, and orientations of same are described in commonly owned U.S. patent application Ser. No. 10/738,608 entitled "Noise Canceling Cardiac Electrodes," filed Dec. 17, 2003, and U.S. patent application Ser. No. 10/465,520 filed Jun. 19, 2003 entitled "Methods And Systems Involving Subcutaneous Electrode Positioning Relative To A Heart", which are hereby incorporated herein by reference.

Certain configurations illustrated herein are generally described as capable of implementing various functions traditionally performed by an implantable cardioverter/defibrillator (ICD), and may operate in numerous cardioversion/defibrillation modes as are known in the art. Exemplary ICD circuitry, structures and functionality, aspects of which may be incorporated in an ITCS device of a type that may benefit from signal separation in accordance with the present invention, are disclosed in commonly owned U.S. Pat. Nos. 5,133,353; 5,179,945; 5,314,459; 5,318,597; 5,620,466; and 5,662,688, which are hereby incorporated herein by reference in their respective entireties.

In particular configurations, systems and methods may perform functions traditionally performed by pacemakers, such as providing various pacing therapies as are known in the art, in addition to cardioversion/defibrillation therapies. Exemplary pacemaker circuitry, structures and functionality, aspects of which may be incorporated in an ITCS device of a type that may benefit from signal separation, are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference in their respective entireties. It is understood that ITCS device configurations may provide for non-physiologic pacing support in addition to, or to the exclusion of, bradycardia and/or anti-tachycardia pacing therapies.

An ITCS device in accordance with the present invention may implement diagnostic and/or monitoring functions as well as provide cardiac stimulation therapy. Exemplary cardiac monitoring circuitry, structures and functionality, aspects of which may be incorporated in an ITCS device of a type that may benefit from signal separation in accordance with the present invention, are disclosed in commonly owned U.S. Pat. Nos. 5,313,953; 5,388,578; and 5,411,031, which are hereby incorporated herein by reference in their respective entireties.

An ITCS device may be used to implement various diagnostic functions, which may involve performing rate-based, pattern and rate-based, and/or morphological tachyarrhythmia discrimination analyses. Subcutaneous, cutaneous, and/or external sensors may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

Figure 1B:
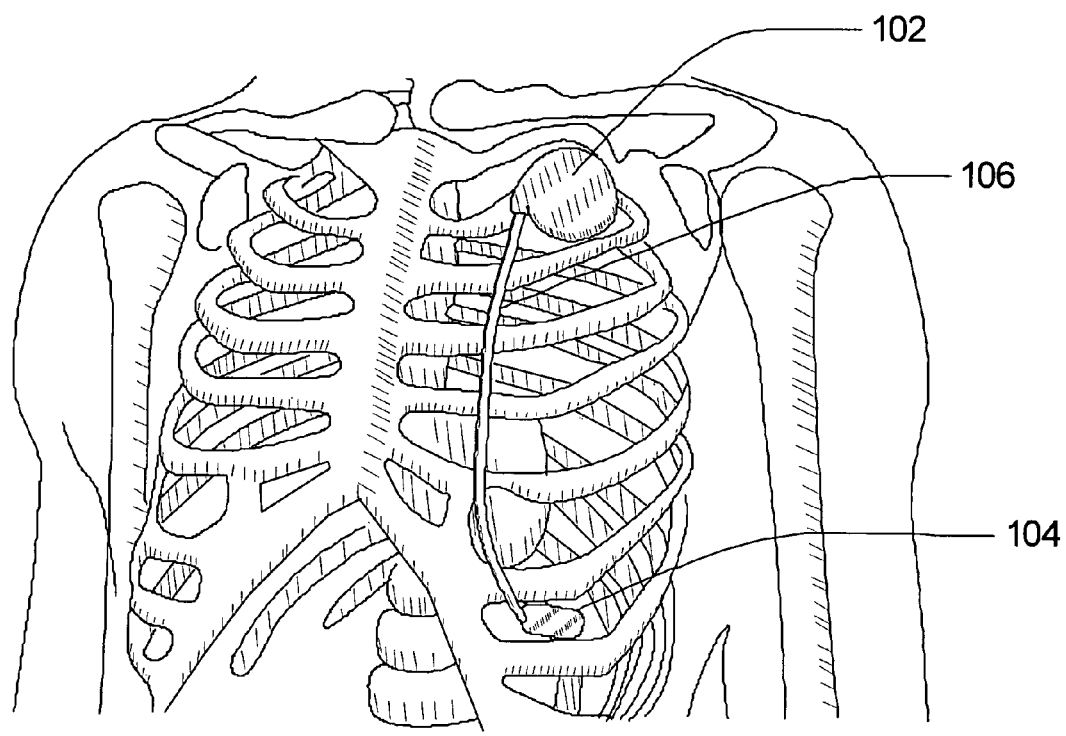

Referring now to FIGS. 1A and 1B of the drawings, there is shown a configuration of a transthoracic cardiac sensing and/or stimulation (ITCS) device having components implanted in the chest region of a patient at different locations. In the particular configuration shown in FIGS. 1A and 1B, the ITCS device includes a housing 102 within which various cardiac sensing, detection, processing, and energy delivery circuitry may be housed. It is understood that the components and functionality depicted in the figures and described herein may be implemented in hardware, software, or a combination of hardware and software. It is further understood that the components and functionality depicted as separate or discrete blocks/elements in the figures may be implemented in combination with other components and functionality, and that the depiction of such components and functionality in individual or integral form is for purposes of clarity of explanation, and not of limitation.

Communications circuitry is disposed within the housing 102 for facilitating communication between the ITCS device and an external communication device, such as a portable or bed-side communication station, patient-carried/worn communication station, or external programmer, for example. The communications circuitry may also facilitate unidirectional or bidirectional communication with one or more external, cutaneous, or subcutaneous physiologic or non-physiologic sensors. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed.

In the configuration shown in FIGS. 1A and 1B, a subcutaneous electrode 104 may be positioned under the skin in the chest region and situated distal from the housing 102. The subcutaneous and, if applicable, housing electrode(s) may be positioned about the heart at various locations and orientations, such as at various anterior and/or posterior locations relative to the heart. The subcutaneous electrode 104 is coupled to circuitry within the housing 102 via a lead assembly 106. One or more conductors (e.g., coils or cables) are provided within the lead assembly 106 and electrically couple the subcutaneous electrode 104 with circuitry in the housing 102. One or more sense, sense/pace or defibrillation electrodes may be situated on the elongated structure of the electrode support, the housing 102, and/or the distal electrode assembly (shown as subcutaneous electrode 104 in the configuration shown in FIGS. 1A and 1B).

In one configuration, the lead assembly 106 is generally flexible and has a construction similar to conventional implantable, medical electrical leads (e.g., defibrillation leads or combined defibrillation/pacing leads). In another configuration, the lead assembly 106 is constructed to be somewhat flexible, yet has an elastic, spring, or mechanical memory that retains a desired configuration after being shaped or manipulated by a clinician. For example, the lead assembly 106 may incorporate a gooseneck or braid system that may be distorted under manual force to take on a desired shape. In this manner, the lead assembly 106 may be shape-fit to accommodate the unique anatomical configuration of a given patient, and generally retains a customized shape after implantation. Shaping of the lead assembly 106 according to this configuration may occur prior to, and during, ITCS device implantation.

In accordance with a further configuration, the lead assembly 106 includes a rigid electrode support assembly, such as a rigid elongated structure that positionally stabilizes the subcutaneous electrode 104 with respect to the housing 102. In this configuration, the rigidity of the elongated structure maintains a desired spacing between the subcutaneous electrode 104 and the housing 102, and a desired orientation of the subcutaneous electrode 104/housing 102 relative to the patient's heart. The elongated structure may be formed from a structural plastic, composite or metallic material, and includes, or is covered by, a biocompatible material. Appropriate electrical isolation between the housing 102 and subcutaneous electrode 104 is provided in cases where the elongated structure is formed from an electrically conductive material, such as metal.

In one configuration, the rigid electrode support assembly and the housing 102 define a unitary structure (e.g., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, the rigid electrode support assembly defines a physically separable unit relative to the housing 102. The rigid electrode support assembly includes mechanical and electrical couplings that facilitate mating engagement with corresponding mechanical and electrical couplings of the housing 102. For example, a header block arrangement may be configured to include both electrical and mechanical couplings that provide for mechanical and electrical connections between the rigid electrode support assembly and housing 102. The header block arrangement may be provided on the housing 102 or the rigid electrode support assembly. Alternatively, a mechanical/electrical coupler may be used to establish mechanical and electrical connections between the rigid electrode support assembly and housing 102. In such a configuration, a variety of different electrode support assemblies of varying shapes, sizes, and electrode configurations may be made available for physically and electrically connecting to a standard ITCS device housing 102.

It is noted that the electrodes and the lead assembly 106 may be configured to assume a variety of shapes. For example, the lead assembly 106 may have a wedge, chevron, flattened oval, or a ribbon shape, and the subcutaneous electrode 104 may include a number of spaced electrodes, such as an array or band of electrodes. Moreover, two or more subcutaneous electrodes 104 may be mounted to multiple electrode support assemblies 106 to achieve a desired spaced relationship amongst subcutaneous electrodes 104.

An ITCS device may incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243, which are hereby incorporated herein by reference in their respective entireties.

Figure 1C:
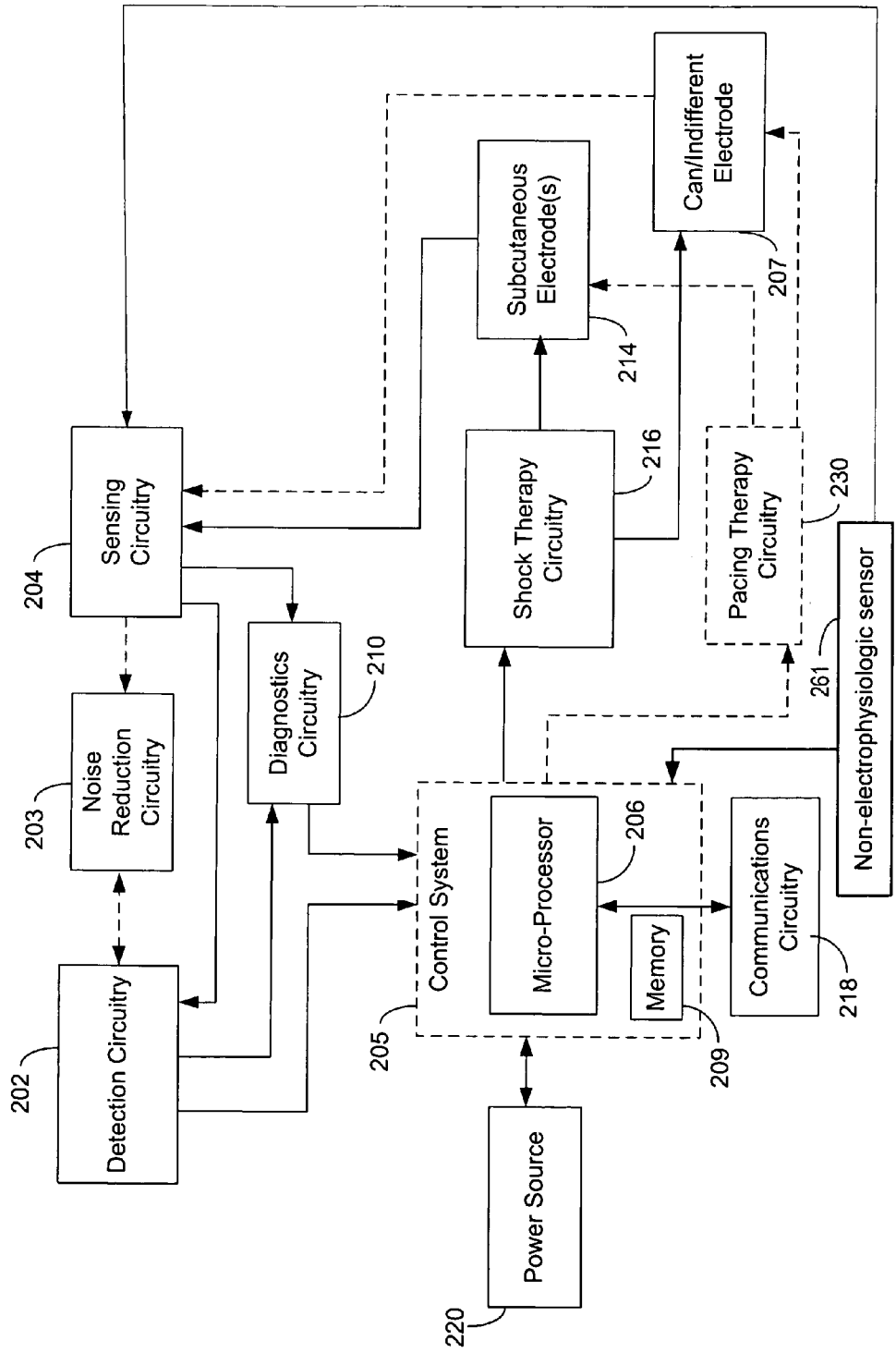
FIG. 1C is a block diagram illustrating various components of a transthoracic cardiac sensing and/or stimulation device in accordance with an embodiment of the present invention.

FIG. 1C is a block diagram depicting various components of an ITCS device in accordance with one configuration. According to this configuration, the ITCS device incorporates a processor-based control system 205 which includes a micro-processor 206 coupled to appropriate memory (volatile and non-volatile) 209, it being understood that any logic-based control architecture may be used. The control system 205 is coupled to circuitry and components to sense, detect, and analyze electrical signals produced by the heart and deliver electrical stimulation energy to the heart under predetermined conditions to treat cardiac arrhythmias. In certain configurations, the control system 205 and associated components also provide pacing therapy to the heart. The electrical energy delivered by the ITCS device may be in the form of low energy pacing pulses or high-energy pulses for cardioversion or defibrillation.

Cardiac signals are sensed using the subcutaneous electrode(s) 214 and the can or indifferent electrode 207 provided on the ITCS device housing. Cardiac signals may also be sensed using only the subcutaneous electrodes 214, such as in a non-active can configuration. As such, unipolar, bipolar, or combined unipolar/bipolar electrode configurations as well as multi-element electrodes and combinations of noise canceling and standard electrodes may be employed. The sensed cardiac signals are received by sensing circuitry 204, which includes sense amplification circuitry and may also include filtering circuitry and an analog-to-digital (A/D) converter. The sensed cardiac signals processed by the sensing circuitry 204 may be received by noise reduction circuitry 203, which may further reduce noise before signals are sent to the detection circuitry 202.

Noise reduction circuitry 203 may also be incorporated after sensing circuitry 202 in cases where high power or computationally intensive noise reduction algorithms are required. The noise reduction circuitry 203, by way of amplifiers used to perform operations with the electrode signals, may also perform the function of the sensing circuitry 204. Combining the functions of sensing circuitry 204 and noise reduction circuitry 203 may be useful to minimize the necessary componentry and lower the power requirements of the system.

In the illustrative configuration shown in FIG. 1C, the detection circuitry 202 is coupled to, or otherwise incorporates, noise reduction circuitry 203. The noise reduction circuitry 203 operates to improve the signal-to-noise ratio (SNR) of sensed cardiac signals by removing noise content of the sensed cardiac signals introduced from various sources. Typical types of transthoracic cardiac signal noise includes electrical noise and noise produced from skeletal muscles, for example.

Detection circuitry 202 typically includes a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 202 to detect and verify the presence and severity of an arrhythmic episode. Exemplary arrhythmia detection and discrimination circuitry, structures, and techniques, aspects of which may be implemented by an ITCS device of a type that may benefit from signal separation in accordance with the present invention, are disclosed in commonly owned U.S. Pat. Nos. 5,301,677 and 6,438,410, which are hereby incorporated herein by reference in their respective entireties.

The detection circuitry 202 communicates cardiac signal information to the control system 205. Memory circuitry 209 of the control system 205 contains parameters for operating in various sensing, defibrillation, and, if applicable, pacing modes, and stores data indicative of cardiac signals received by the detection circuitry 202. The memory circuitry 209 may also be configured to store historical ECG and therapy data, which may be used for various purposes and transmitted to an external receiving device as needed or desired.

In certain configurations, the ITCS device may include diagnostics circuitry 210. The diagnostics circuitry 210 typically receives input signals from the detection circuitry 202 and the sensing circuitry 204. The diagnostics circuitry 210 provides diagnostics data to the control system 205, it being understood that the control system 205 may incorporate all or part of the diagnostics circuitry 210 or its functionality. The control system 205 may store and use information provided by the diagnostics circuitry 210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 205 processes cardiac signal data received from the detection circuitry 202 and initiates appropriate tachyarrhythmia therapies to terminate cardiac arrhythmic episodes and return the heart to normal sinus rhythm. The control system 205 is coupled to shock therapy circuitry 216. The shock therapy circuitry 216 is coupled to the subcutaneous electrode(s) 214 and the can or indifferent electrode 207 of the ITCS device housing. Upon command, the shock therapy circuitry 216 delivers cardioversion and defibrillation stimulation energy to the heart in accordance with a selected cardioversion or defibrillation therapy. In a less sophisticated configuration, the shock therapy circuitry 216 is controlled to deliver defibrillation therapies, in contrast to a configuration that provides for delivery of both cardioversion and defibrillation therapies. Exemplary ICD high energy delivery circuitry, structures and functionality, aspects of which may be incorporated in an ITCS device of a type that may benefit from aspects of the present invention are disclosed in commonly owned U.S. Pat. Nos. 5,372,606; 5,411,525; 5,468,254; and 5,634,938, which are hereby incorporated herein by reference in their respective entireties.

In accordance with another configuration, an ITCS device may incorporate a cardiac pacing capability in addition to cardioversion and/or defibrillation capabilities. As is shown in dotted lines in FIG. 1C, the ITCS device may include pacing therapy circuitry 230, which is coupled to the control system 205 and the subcutaneous and can/indifferent electrodes 214, 207. Upon command, the pacing therapy circuitry delivers pacing pulses to the heart in accordance with a selected pacing therapy. Control signals, developed in accordance with a pacing regimen by pacemaker circuitry within the control system 205, are initiated and transmitted to the pacing therapy circuitry 230 where pacing pulses are generated. A pacing regimen may be modified by the control system 205.

A number of cardiac pacing therapies may be useful in a transthoracic cardiac monitoring and/or stimulation device. Such cardiac pacing therapies may be delivered via the pacing therapy circuitry 230 as shown in FIG. 1C. Alternatively, cardiac pacing therapies may be delivered via the shock therapy circuitry 216, which effectively obviates the need for separate pacemaker circuitry.

The ITCS device shown in FIG. 1C is configured to receive signals from one or more physiologic and/or non-physiologic sensors in accordance with embodiments of the present invention. Depending on the type of sensor employed, signals generated by the sensors may be communicated to transducer circuitry coupled directly to the detection circuitry 202 or indirectly via the sensing circuitry 204. It is noted that certain sensors may transmit sense data to the control system 205 without processing by the detection circuitry 202.

Non-electrophysiological cardiac sensors may be coupled directly to the detection circuitry 202 or indirectly via the sensing circuitry 204. Non-electrophysiological cardiac sensors sense cardiac activity that is non-electrophysiological in nature. Examples of non-electrophysiological cardiac sensors are blood oxygen sensors, blood volume sensors, acoustic sensors and/or pressure transducers, and accelerometers. Signals from these sensors are developed based on cardiac activity, but are not derived directly from electrophysiological sources (e.g., R-waves or P-waves). A non-electrophysiological cardiac sensor 261, as is illustrated in FIG. 1C, may be connected to one or more of the sensing circuitry 204, detection circuitry 202 (connection not shown for clarity), and the control system 205.

Communications circuitry 218 is coupled to the microprocessor 206 of the control system 205. The communications circuitry 218 allows the ITCS device to communicate with one or more receiving devices or systems situated external to the ITCS device. By way of example, the ITCS device may communicate with a patient-worn, portable or bedside communication system via the communications circuitry 218. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the ITCS device via the communications circuitry 218. It is noted that physiologic or non-physiologic sensors equipped with wireless transmitters or transceivers may communicate with a receiving system external of the patient.

The communications circuitry 218 may allow the ITCS device to communicate with an external programmer. In one configuration, the communications circuitry 218 and the programmer unit (not shown) use a wire loop antenna and a radio frequency telemetric link, as is known in the art, to receive and transmit signals and data between the programmer unit and communications circuitry 218. In this manner, programming commands and data are transferred between the ITCS device and the programmer unit during and after implant. Using a programmer, a physician is able to set or modify various parameters used by the ITCS device. For example, a physician may set or modify parameters affecting sensing, detection, pacing, and defibrillation functions of the ITCS device, including pacing and cardioversion/defibrillation therapy modes.

Typically, the ITCS device is encased and hermetically sealed in a housing suitable for implanting in a human body as is known in the art. Power to the ITCS device is supplied by an electrochemical power source 220 housed within the ITCS device. In one configuration, the power source 220 includes a rechargeable battery. According to this configuration, charging circuitry is coupled to the power source 220 to facilitate repeated non-invasive charging of the power source 220. The communications circuitry 218, or separate receiver circuitry, is configured to receive RF energy transmitted by an external RF energy transmitter. The ITCS device may, in addition to a rechargeable power source, include a non-rechargeable battery. It is understood that a rechargeable power source need not be used, in which case a long-life non-rechargeable battery is employed.

Figure 1D:
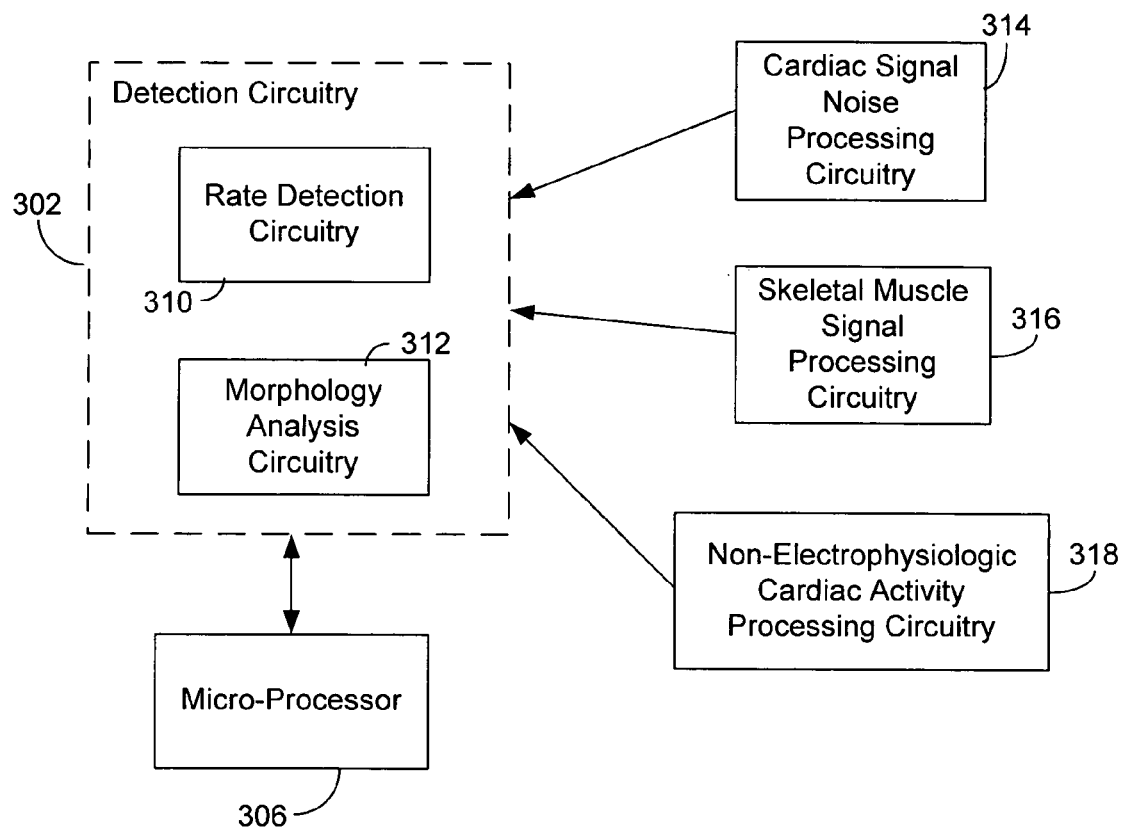
FIG. 1D is a block diagram illustrating various processing and detection components of a transthoracic cardiac sensing and/or stimulation device in accordance with an embodiment of the present invention.

FIG. 1D illustrates a configuration of detection circuitry 302 of an ITCS device, which includes one or both of rate detection circuitry 310 and morphological analysis circuitry 312. Detection and verification of arrhythmias may be accomplished using rate-based discrimination algorithms as known in the art implemented by the rate detection circuitry 310. Arrhythmic episodes may also be detected and verified by morphology-based analysis of sensed cardiac signals as is known in the art. Tiered or parallel arrhythmia discrimination algorithms may also be implemented using both rate-based and morphologic-based approaches. Further, a rate and pattern-based arrhythmia detection and discrimination approach may be employed to detect and/or verify arrhythmic episodes, such as the approach disclosed in U.S. Pat. Nos. 6,487,443; 6,259,947; 6,141,581; 5,855,593; and 5,545,186, which are hereby incorporated herein by reference in their respective entireties.

The detection circuitry 302, which is coupled to a microprocessor 306, may be configured to incorporate, or communicate with, specialized circuitry for processing sensed cardiac signals in manners particularly useful in a transthoracic cardiac sensing and/or stimulation device. As is shown by way of example in FIG. 1D, the detection circuitry 302 may receive information from multiple physiologic and non-physiologic sensors. As illustrated, transthoracic acoustics may be monitored using an appropriate acoustic sensor. Heart sounds, for example, may be detected and processed by non-electrophysiologic cardiac sensor processing circuitry 318 for a variety of purposes. The acoustics data is transmitted to the detection circuitry 302, via a hardwire or wireless link, and used to enhance cardiac signal detection. For example, acoustic information may be used in accordance with the present invention to quickly identify a cardiac signal within a group of separated signals, such as signals separated from a composite signal using a blind source separation technique or a linear signal separation technique.

The detection circuitry 302 may also receive information from one or more sensors that monitor skeletal muscle activity. In addition to cardiac activity signals, transthoracic electrodes readily detect skeletal muscle signals. Such skeletal muscle signals may be used to determine the activity level of the patient. In the context of cardiac signal detection, such skeletal muscle signals are considered artifacts of the cardiac activity signal, which may be viewed as noise. Processing circuitry 316 receives signals from one or more skeletal muscle sensors, and transmits processed skeletal muscle signal data to the detection circuitry 302. This data may be used to discriminate normal cardiac sinus rhythm with skeletal muscle noise from cardiac arrhythmias.

As was previously discussed, the detection circuitry 302 is coupled to, or otherwise incorporates, noise-processing circuitry 314. The noise processing circuitry 314 processes sensed cardiac signals to improve the SNR of sensed cardiac signals by reducing noise content of the sensed cardiac signals.

The components, functionality, and structural configurations depicted in FIGS. 1A-1D are intended to provide an understanding of various features and combination of features that may be incorporated in an ITCS device. It is understood that a wide variety of ITCS and other implantable cardiac monitoring and/or stimulation device configurations are contemplated, ranging from relatively sophisticated to relatively simple designs. As such, particular ITCS or cardiac monitoring and/or stimulation device configurations may include particular features as described herein, while other such device configurations may exclude particular features described herein.

In accordance with embodiments of the invention, an ITCS device may be implemented to include a subcutaneous electrode system that provides for one or both of cardiac sensing and arrhythmia therapy delivery. According to one approach, an ITCS device may be implemented as a chronically implantable system that performs monitoring, diagnostic and/or therapeutic functions. The ITCS device may automatically detect and treat cardiac arrhythmias. In one configuration, the ITCS device includes a pulse generator and one or more electrodes that are implanted subcutaneously in the chest region of the body, such as in the anterior thoracic region of the body. The ITCS device may be used to provide atrial and ventricular therapy for bradycardia and tachycardia arrhythmias. Tachyarrhythmia therapy may include cardioversion, defibrillation and anti-tachycardia pacing (ATP), for example, to treat atrial or ventricular tachycardia or fibrillation. Bradycardia therapy may include temporary post-shock pacing for bradycardia or asystole. Methods and systems for implementing post-shock pacing for bradycardia or asystole are described in commonly owned U.S. Patent Application entitled "Subcutaneous Cardiac Stimulator Employing Post-Shock Transthoracic Asystole Prevention Pacing, Ser. No. 10/377,274, filed on Feb. 28, 2003, which is incorporated herein by reference in its entirety.

In one configuration, an ITCS device according to one approach may utilize conventional pulse generator and subcutaneous electrode implant techniques. The pulse generator device and electrodes may be chronically implanted subcutaneously. Such an ITCS may be used to automatically detect and treat arrhythmias similarly to conventional implantable systems. In another configuration, the ITCS device may include a unitary structure (e.g., a single housing/unit). The electronic components and electrode conductors/connectors are disposed within or on the unitary ITCS device housing/electrode support assembly.

The ITCS device contains the electronics and may be similar to a conventional implantable defibrillator. High voltage shock therapy may be delivered between two or more electrodes, one of which may be the pulse generator housing (e.g., can), placed subcutaneously in the thoracic region of the body.

Additionally or alternatively, the ITCS device may also provide lower energy electrical stimulation for bradycardia therapy. The ITCS device may provide brady pacing similarly to a conventional pacemaker. The ITCS device may provide temporary post-shock pacing for bradycardia or asystole. Sensing and/or pacing may be accomplished using sense/pace electrodes positioned on an electrode subsystem also incorporating shock electrodes, or by separate electrodes implanted subcutaneously.

The ITCS device may detect a variety of physiological signals that may be used in connection with various diagnostic, therapeutic or monitoring implementations. For example, the ITCS device may include sensors or circuitry for detecting respiratory system signals, cardiac system signals, and signals related to patient activity. In one embodiment, the ITCS device senses intrathoracic impedance, from which various respiratory parameters may be derived, including, for example, respiratory tidal volume and minute ventilation. Sensors and associated circuitry may be incorporated in connection with an ITCS device for detecting one or more body movement or body position related signals. For example, accelerometers and GPS devices may be employed to detect patient activity, patient location, body orientation, or torso position.

The ITCS device may be used within the structure of an advanced patient management (APM) system. Advanced patient management systems may allow physicians to remotely and automatically monitor cardiac and respiratory functions, as well as other patient conditions. In one example, implantable cardiac rhythm management systems, such as cardiac pacemakers, defibrillators, and resynchronization devices, may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

An ITCS device according to one approach provides an easy to implant therapeutic, diagnostic or monitoring system. The ITCS system may be implanted without the need for intravenous or intrathoracic access, providing a simpler, less invasive implant procedure and minimizing lead and surgical complications. In addition, this system would have advantages for use in patients for whom transvenous lead systems cause complications. Such complications include, but are not limited to, surgical complications, infection, insufficient vessel patency, complications associated with the presence of artificial valves, and limitations in pediatric patients due to patient growth, among others. An ITCS system according to this approach is distinct from conventional approaches in that it may be configured to include a combination of two or more electrode subsystems that are implanted subcutaneously in the anterior thorax.

Figure 2:
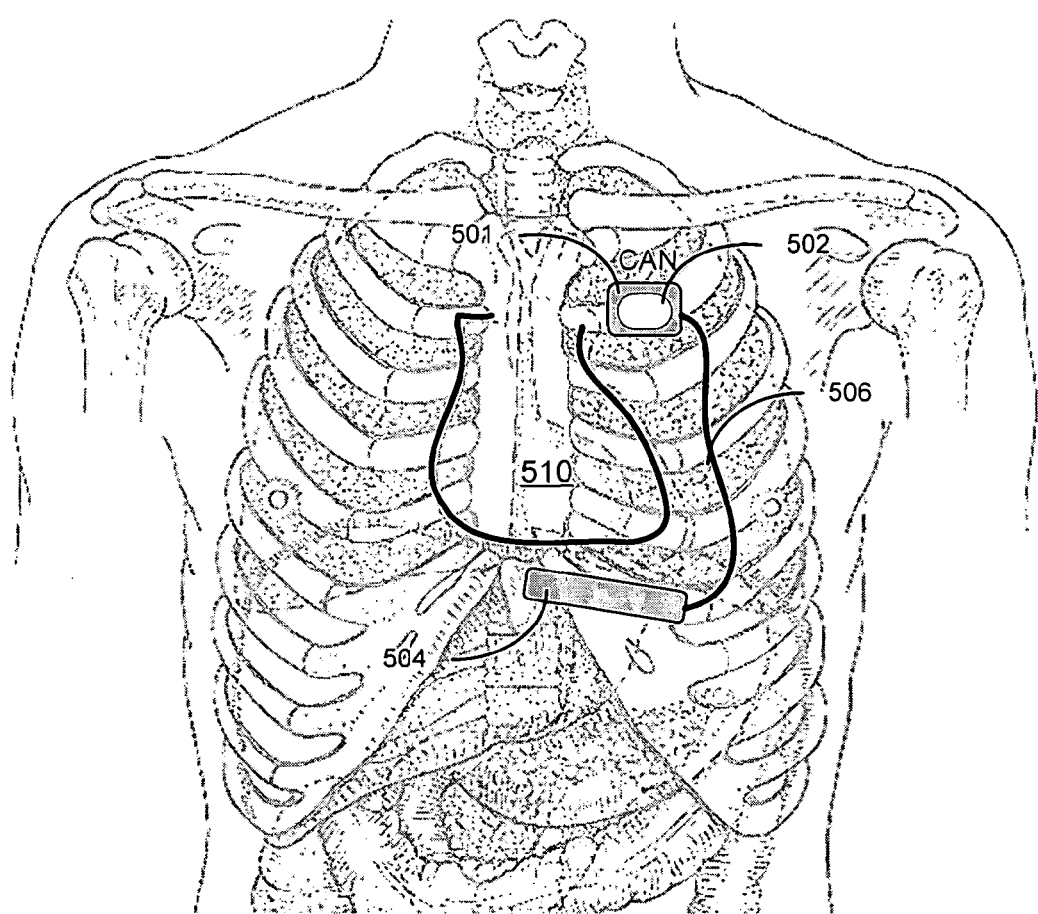
FIG. 2 is a diagram illustrating components of a transthoracic cardiac sensing and/or stimulation device including an electrode array in accordance with an embodiment of the present invention.

In one configuration, as is illustrated in FIG. 2, electrode subsystems of an ITCS system are arranged about a patient's heart 510. The ITCS system includes a first electrode subsystem, comprising a can electrode 502, and a second electrode subsystem 504 that includes at least two electrodes or at least one multi-element electrode. The second electrode subsystem 504 may include a number of electrodes used for sensing and/or electrical stimulation.

In various configurations, the second electrode subsystem 504 may include a combination of electrodes. The combination of electrodes of the second electrode subsystem 504 may include coil electrodes, tip electrodes, ring electrodes, multi-element coils, spiral coils, spiral coils mounted on non-conductive backing, screen patch electrodes, and other electrode configurations. A suitable non-conductive backing material is silicone rubber, for example.

The can electrode 502 is positioned on the housing 501 that encloses the ITCS device electronics. In one embodiment, the can electrode 502 includes the entirety of the external surface of housing 501. In other embodiments, various portions of the housing 501 may be electrically isolated from the can electrode 502 or from tissue. For example, the active area of the can electrode 502 may include all or a portion of either the anterior or posterior surface of the housing 501 to direct current flow in a manner advantageous for cardiac sensing and/or stimulation.

In accordance with one embodiment, the housing 501 may resemble that of a conventional implantable ICD, is approximately 20-100 cc in volume, with a thickness of 0.4 to 2 cm and with a surface area on each face of approximately 30 to 100 $cm^2$. As previously discussed, portions of the housing may be electrically isolated from tissue to optimally direct current flow. For example, portions of the housing 501 may be covered with a non-conductive, or otherwise electrically resistive, material to direct current flow. Suitable non-conductive material coatings include those formed from silicone rubber, polyurethane, or parylene, for example.

In addition, or alternatively, all or portions of the housing 501 may be treated to change the electrical conductivity characteristics thereof for purposes of optimally directing current flow. Various known techniques may be employed to modify the surface conductivity characteristics of the housing 501, such as by increasing or decreasing surface conductivity, to optimize current flow. Such techniques may include those that mechanically or chemically alter the surface of the housing 501 to achieve desired electrical conductivity characteristics.

As was discussed above, cardiac signals collected from subcutaneously implanted electrodes may be corrupted by noise. In addition, certain noise sources have frequency characteristics similar to those of the cardiac signal. Such noise may lead to over sensing and spurious shocks. Due to the possibility of relatively high amplitude of the noise signal and overlapping frequency content, filtering alone does not lead to complete suppression of the noise. In addition, filter performance is not generally sufficiently robust against the entire class of noises encountered. Further, known adaptive filtering approaches require a reference signal that is often unknown for situations when a patient experiences VF or high amplitude noise.

In accordance with one approach of the present invention, an ITCS device may be implemented to identify cardiac signals within a group of separated signals, such as those obtained from a blind source separation (BSS) technique. It is understood that all or certain aspects of the signal identification technique described below may be implemented in a device or system (implantable or non-implantable) other than an ITCS device, and that the description of the BSS technique as the method separation implemented in an ITCS device is provided for purposes of illustration, and not of limitation. Devices and methods of blind source separation are further described in commonly owned U.S. patent application Ser. No. 10/741,814, filed Dec. 19, 2003, hereby incorporated herein by reference. Devices and methods associated with another useful signal separation approach that uses noise canceling electrodes are further described in commonly owned U.S. patent application Ser. No. 10/738,608, filed Dec. 17, 2003, hereby incorporated herein by reference.

Signal separation techniques provide for separation of many individual signals from composite signals. For example, a composite signal detected on or within a patient may contain several signal components produced from a variety of signal sources, such signal components including cardiac signals, skeletal muscle movement related signals, electromagnetic interference signals, and signals of unknown origin. Signal separation techniques separate the composite signal into individual signals, but do not necessarily indicate the source of such signals.

As is disclosed in previously incorporated U.S. patent application Ser. No. 10/741,814, the use of the largest eigenvalues produced by performing a principal component analysis on a composite signal matrix provides one method of identifying the separated signals most likely to be the cardiac signal of interest for ITCS devices. However, analyzing all the separated signals is a computationally intensive operation. The present invention provides an indication of the signals most likely to be the cardiac signal of interest in an efficient manner, thereby greatly decreasing the time necessary to identify the cardiac signal of interest from many possible separated signals.

Figure 3:
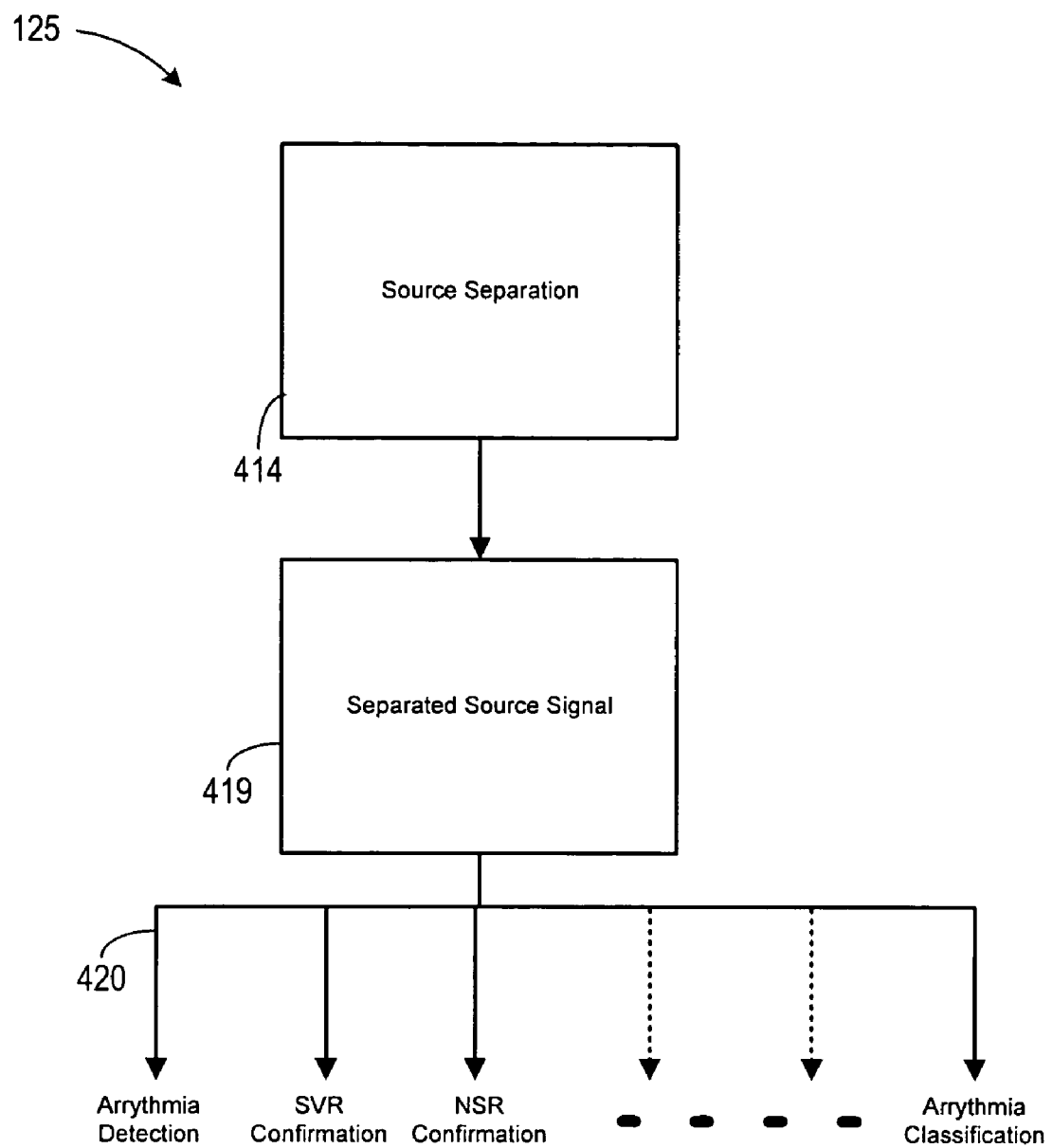
FIG. 3 is a block diagram illustrating uses of signal separation in accordance with the present invention.
Figure 4:
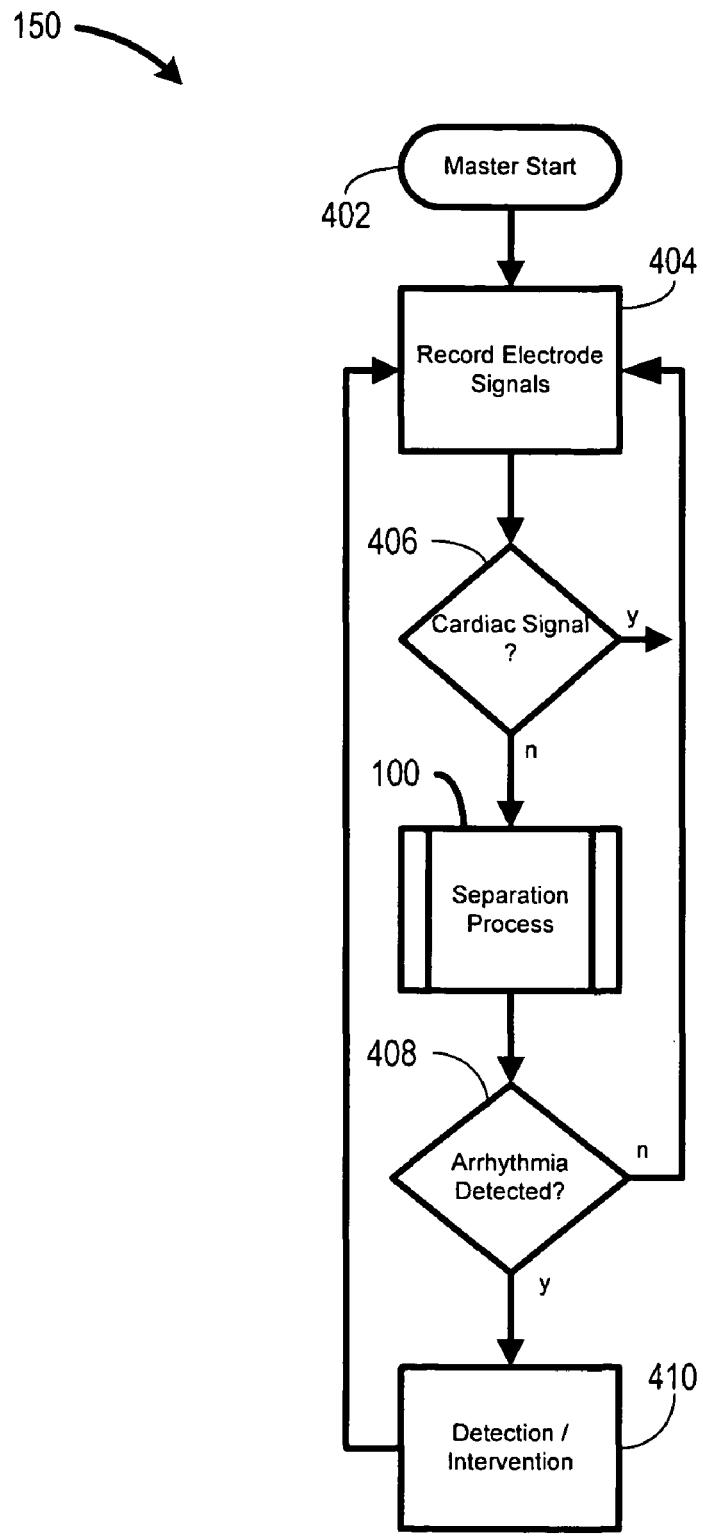
FIG. 4 is a block diagram of a cardiac sensing methodology incorporating signal separation in accordance with the present invention.
Figure 5:
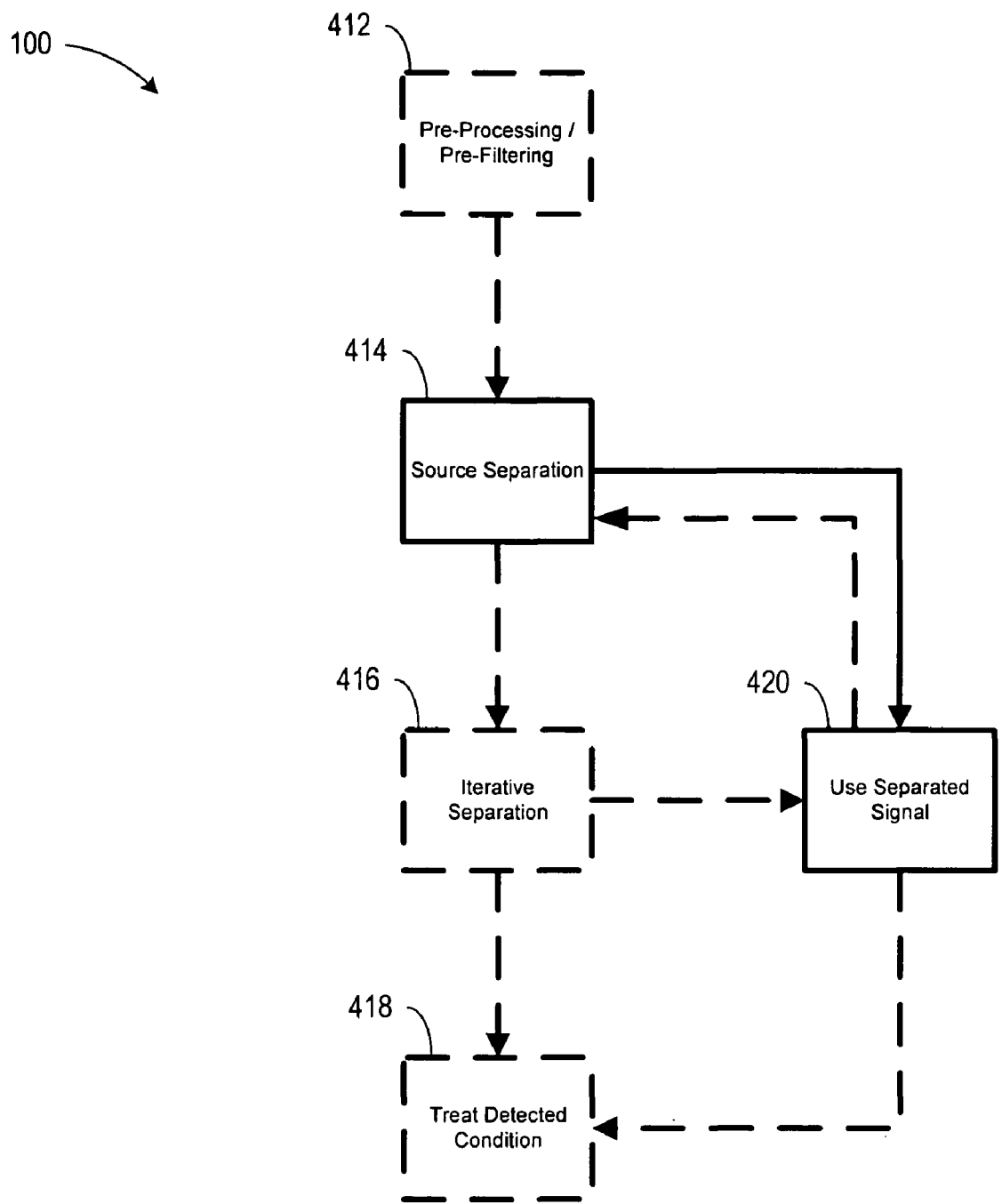
FIG. 5 is a block diagram of a signal separation process in accordance with the present invention.

Referring now to FIGS. 3 through 5, subcutaneous cardiac sensing and/or stimulation devices and methods employing cardiac signal separation are described, which may be used to separate signals to discriminate and/or identify a signal of interest within the separated signals. The main principle of signal separation rests on the premise that spatially distributed electrodes collect components of a signal from a common origin (e.g., the heart) with the result that these components are strongly correlated to each other in time. In addition, these components may also be weakly correlated to components of another origin (e.g., noise). An ITCS device may be implemented to separate these components according to their sources. To achieve this, the methods and algorithms illustrated in FIGS. 3 through 5 may be implemented.

FIG. 3 illustrates a signal separation system 125 in accordance with the present invention. A signal separation process 414 is performed, providing a separated signal 419. The separated signal 419 is available for a variety of uses 420, such as arrhythmia detection, SVR (Supra-Ventricular Rhythm) confirmation, NSR (Normal Sinus Rhythm) confirmation, arrhythmia classification or other use.

FIG. 4 illustrates a signal separation methodology 150 in accordance with the present invention. After initiating 402 the methodology, a signal record process begins 404. During the signal record event 404, one or more electrode signals are recorded for later processing, such as by signal separation processing. The recording may be continuous or performed for a given period of time. At block 406, a determination is made as to the presence or absence of an SVR using technology known in the art. If an SVR is detected, no other action is necessary, and recording and evaluation for SVR continues.

If SVR is absent, it is desirable to determine whether an adverse cardiac condition exists, necessitating intervention, or whether there is simply a spurious signal loss or other event not necessitating intervention. A loss of SVR at decision 406 initiates a separation process 100. After the separation process 100 and any intervention steps deemed necessary are completed, a determination 408 is made as to whether other processing is necessary. If no further processing is necessary, the recording process 404 continues. If further processing is necessary, such additional processing 410 is performed, along with any further action associated with processing 410, and then recording 404 continues.

FIG. 5 illustrates another embodiment of a signal separation process 100. A set of composite signals, including at least two and up to n signals, are selected for separation, where n is an integer. Each electrode provides a composite signal associated with an unknown number of sources. Pre-processing and/or pre-filtering 412 can be performed on each of the composite signals. It may be advantageous to filter each composite signal using the same filtering function. Signal separation 414 is performed, providing at least one separated signal. The separated signal can then be used 420 for some specified purpose, such as to confirm a normal sinus rhythm, determine a cardiac condition, define a noise signal, or other desired use.

If a treatment is desired, an appropriate treatment or therapy 418 is performed. If continued signal separation is desired, the process returns to perform such signal separation 414 and may iteratively separate 416 more signals until a desired signal is found, or all signals are separated.

If there is no clear candidate cardiac signal, a process in accordance with the present invention may be used to quickly search for the signal of interest (e.g., cardiac signal). This process may be repeated until such a signal is found, or no more signals are separable as determined by exceeding a predefined number of iterations, or some other termination criterion.

Figure 6:
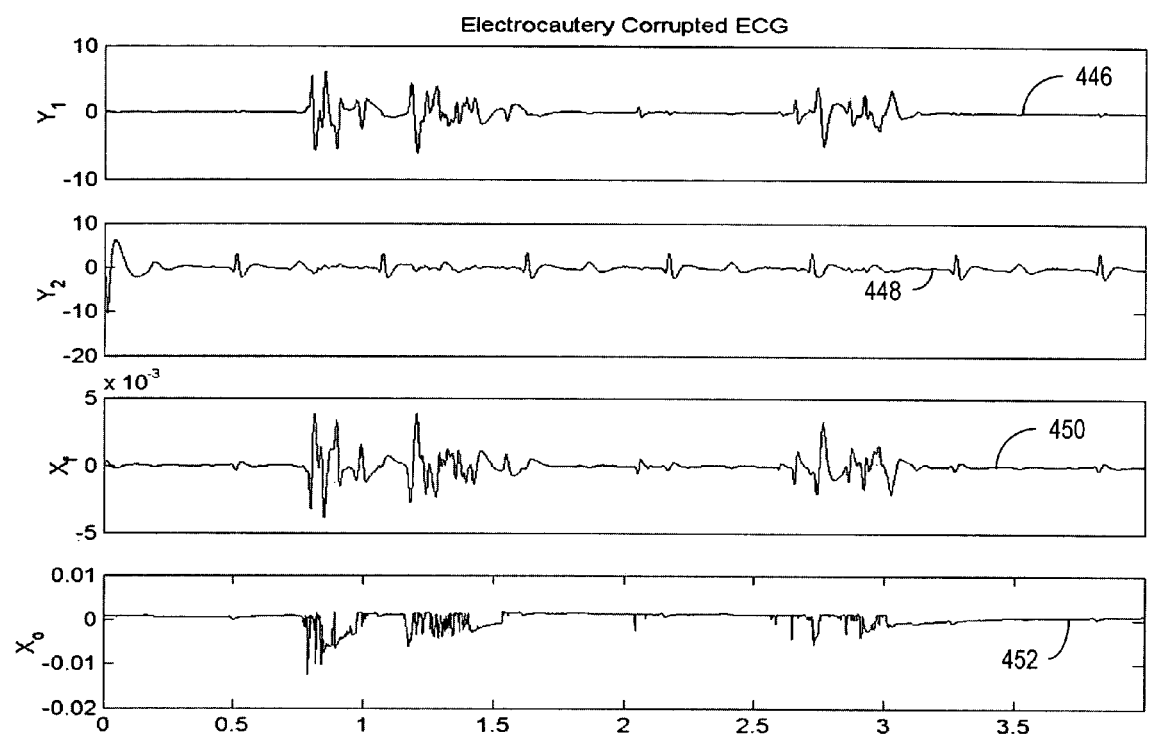
FIG. 6 is a graph illustrating the results of a signal separation process in accordance with the present invention.

FIG. 6 graphically depicts cardiac SNR improvement achievable by a signal separation methodology in accordance with the principles of the present invention. In this illustrative example, data was gathered under low-SNR conditions with electrocautery noise using seven electrodes implanted in the thoracic region of a pig. The bottom subplot, identified as trace 452, represents the raw implanted electrode signal. The next subplot, identified as trace 450, shows this signal after input filtering for optimal raw SNR using a linear-phase ($4^{th}$-order Bessel) band pass filter from 5 to 20 Hz. The top two subplots, identified as trace 448 and trace 446, illustrate the resulting separated components associated with the two largest eigenvalues. In this example, trace 446 is associated with the electrocautery signal, having the largest eigenvalue. Trace 448 is the uncorrupted cardiac signal.

An ITCS device may, for example, employ a hierarchical decision-making procedure that initiates a blind source separation algorithm when noise or possible arrhythmia is detected. By way of example, a local peak density algorithm or a curvature-based significant point methodology may be used as a high-level detection routine.

The cardiac signal may be identified among the few (e.g., two or three) largest separated signals, however examining the entirety of all candidate signals is computationally intensive. Information from a non-electrophysiologic sensor, such as those described earlier, may be used to focus the search for the cardiac signal among the candidate signals. A signal independent of cardiac electrical activity, such as an acoustic signal of cardiac heart-sounds, an accelerometer, a blood sensor, or other non-electrophysiologic source sensor, may be used to improve the detection and classification of the cardiac signal from the separated signals.

In an embodiment of the present invention, heart sounds are used to aid in signal discrimination when detecting various heart rhythms in the presence of electrical noise and/or artifacts. Because the additional discriminating non-electrophysiologic signal is time correlated with respect to the cardiac electrophysiological signals, the non-electrophysiologic signal may provide information about a patient's rhythm state even in the presence of electrical noise.

In one embodiment, a subcutaneous sensor, such as an accelerometer or acoustic transducer, may be used to detect heart sounds. The heart sounds may be used together with rate, curvature, and other ECG information to discriminate normal sinus with electrical noise from potentially lethal arrhythmias such as ventricular tachycardia and ventricular fibrillation. An ITCS device may utilize one or more of the presence, characteristics, and frequency of occurrence of the heart sound combined with ECG information when performing signal or rhythm discrimination.

A heart rate determined from the ECG signal may, for example, be analyzed along with heart sound information for diagnostic purposes. High ECG heart rate detection along with normal rate heart sounds would indicate the presence of noise in the ECG signal. High ECG heart rate detection along with modified heart sounds would indicate a potentially lethal arrhythmia. It is noted that ECG morphology or other techniques could replace rate in the example above. It should also be noted that other sensor derived signals could replace heart sounds. For example, impedance, pulse pressure, blood volume/flow, or cardiac accelerations could be used.

Various types of acoustic sensors may be used to detect heart sounds. Examples of such acoustic sensors include diaphragm based acoustic sensors, MEMS-based acoustic sensors such as a MEMS-based acoustic transducer, fiber optic acoustic sensors, piezoelectric sensors, and accelerometer based acoustic sensors and arrays. These sensors may be used to detect the audio frequency pressure waves associated with the heart sounds, and may also be used to detect other non-electrophysiologic cardiac related signals.

Figure 7:
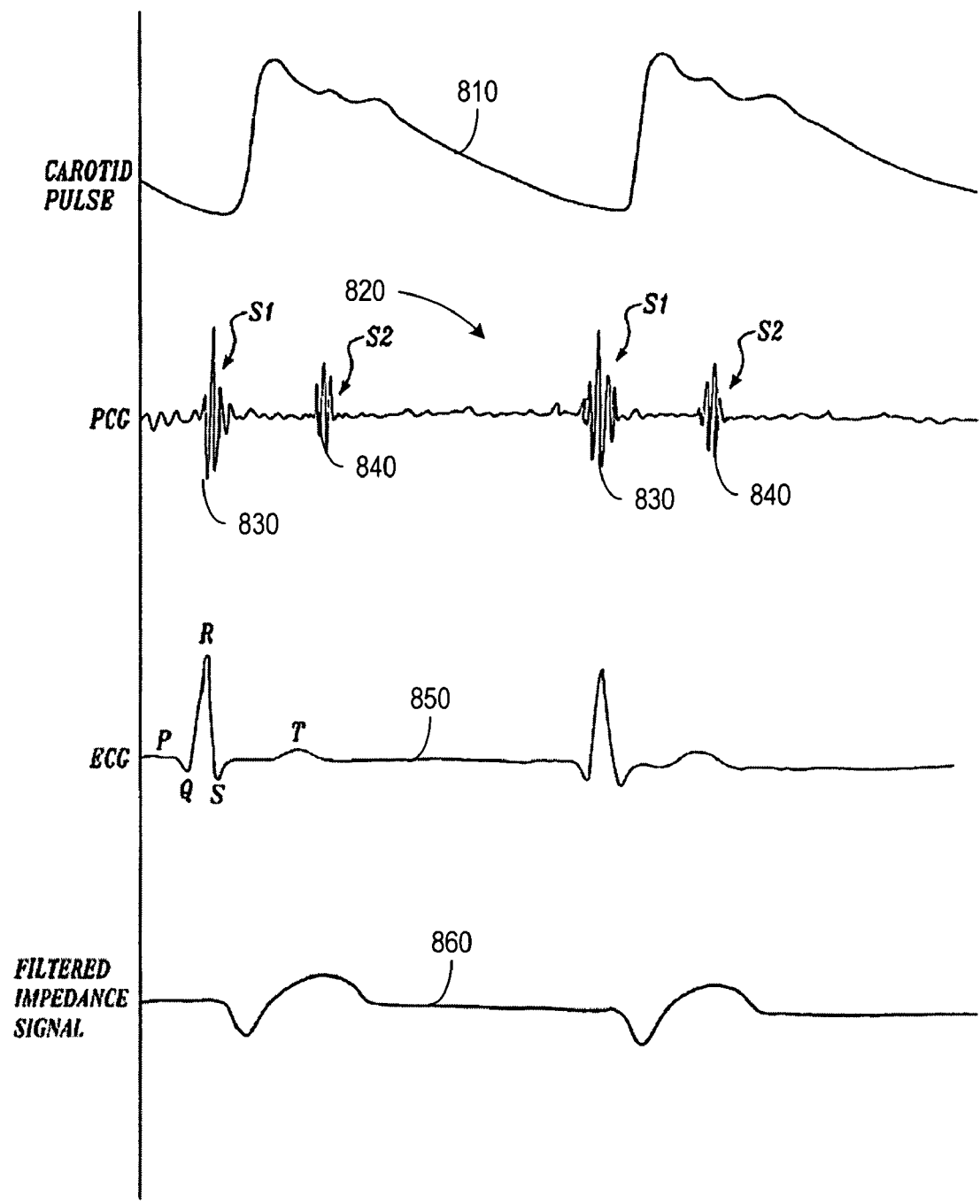
FIG. 7 is a pictorial diagram of a carotid pulse waveform, a phonocardiogram (PCG) waveform, an electrocardiogram (ECG) waveform, and a filtered transthoracic impedance signal for two consecutive heartbeats.

The presence of cardiac pulse, or heartbeat, in a patient is generally detected by palpating the patient's neck and sensing changes in the volume of the patient's carotid artery due to blood pumped from the patient's heart. A graph of a carotid pulse signal 810, representative of the physical expansion and contraction of a patient's carotid artery during two consecutive pulses, or heartbeats, is shown at the top of FIG. 7. When the heart's ventricles contract during a heartbeat, a pressure wave is sent throughout the patient's peripheral circulation system. The carotid pulse signal 810 shown in FIG. 7 rises with the ventricular ejection of blood at systole and peaks when the pressure wave from the heart reaches a maximum. The carotid pulse signal 810 falls off again as the pressure subsides toward the end of each pulse.

The opening and closing of the patient's heart valves during a heartbeat causes high-frequency vibrations in the adjacent heart wall and blood vessels. These vibrations can be heard in the patient's body as heart sounds, and may be detected by sensors, as described earlier. A conventional phonocardiogram (PCG) transducer placed on a patient converts the acoustical energy of the heart sounds to electrical energy, resulting in a PCG waveform 820 that may be recorded and displayed, as shown by the graph in the upper middle portion of FIG. 7.

As indicated by the PCG waveform 820 shown in FIG. 7, a typical heartbeat produces two main heart sounds. A first heart sound 830, denoted S1, is generated by vibration generally associated with the closure of the tricuspid and mitral valves at the beginning of systole. Typically, the heart sound 830 is about 14 milliseconds long and contains frequencies up to approximately 500 Hz. A second heart sound 840, denoted S2, is generally associated with vibrations resulting from the closure of the aortic and pulmonary valves at the end of systole. While the duration of the second heart sound 840 is typically shorter than the first heart sound 830, the spectral bandwidth of the second heart sound 840 is typically larger than that of the first heart sound 830.

An electrocardiogram (ECG) waveform 850 describes the electrical activity of a patient's heart. The graph in the lower middle portion of FIG. 7 illustrates an example of the ECG waveform 850 for two heartbeats and corresponds in time with the carotid pulse signal 810 and PCG waveform 820 also shown in FIG. 7. Referring to the first shown heartbeat, the portion of the ECG waveform 850 representing depolarization of the atrial muscle fibers is referred to as the "P" wave. Depolarization of the ventricular muscle fibers is collectively represented by the "Q," "R," and "S" waves of the ECG waveform, referred to as the QRS complex. Finally, the portion of the waveform representing repolarization of the ventricular muscle fibers is known as the "T" wave. Between heartbeats, the ECG waveform 850 returns to an isopotential level.

Fluctuations in a patient's transthoracic impedance signal 860 also correlate with blood flow that occurs with each cardiac pulse wave. The bottom graph of FIG. 7 illustrates an example of a filtered transthoracic impedance signal 860 for a patient in which fluctuations in impedance correspond in time with the carotid pulse signal 810, the PCG waveform 820, and ECG waveform 850, also shown in FIG. 7.

Figure 8:
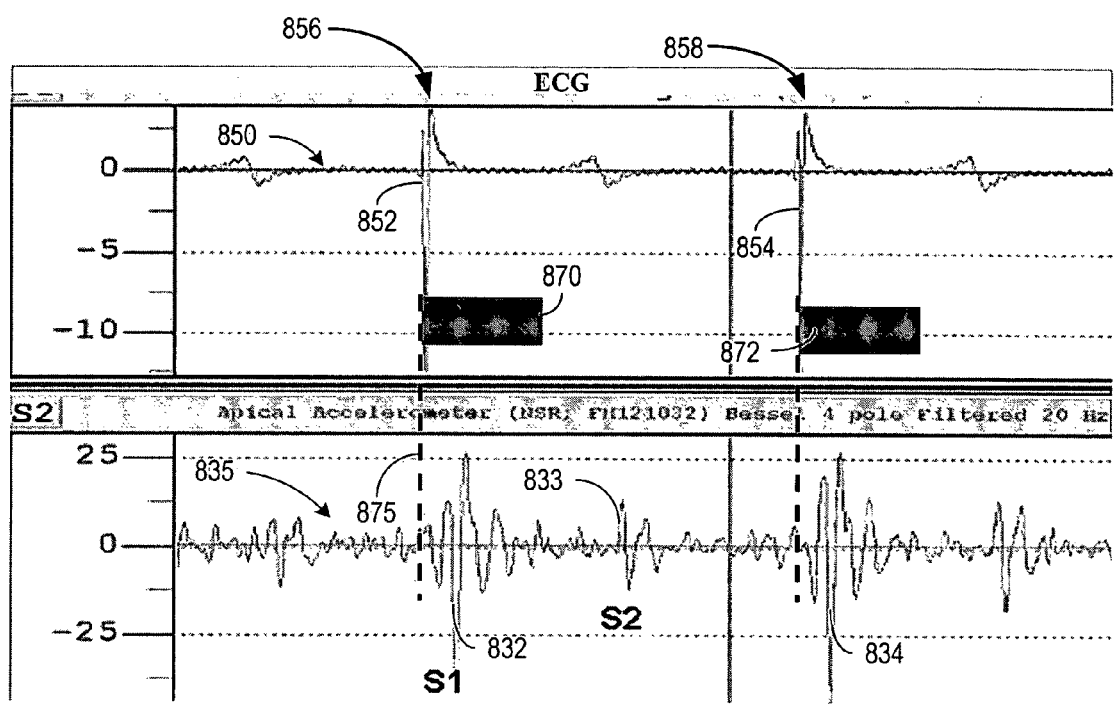
FIG. 8 is a graph illustrating two consecutive pseudo PQRS complexes and their associated pseudo accelerometer signals, and a detection window for correlation of the signals in accordance with an embodiment of the present invention.

Referring now to FIG. 8, in another embodiment of the present invention involving heart sounds, such sounds may be used for selection of separated signals. In general terms, this approach provides for selection of the ECG signal from a group of separated signals. A blind source separation (BSS) technique may be employed, it being understood that other signal separation techniques that provide for a separated cardiac signal from a set of detected signals may be used (e.g., the technique described in previously incorporated U.S. patent application Ser. No. 10/738,608). This technique can separate cardiac signals from noise and artifacts in a cardiac monitoring system (either external or implantable), such as an ITCS device for example. The BSS technique is used to separate signals, and, in a primitive form, provides no information as to which signal is the cardiac signal. This information may be derived from other algorithms following the BSS signal separation operation, such as by use of a heart sound signal or other non-electrophysiologic signal.

FIG. 8 is a graph illustrating two consecutive PQRS complexes in the ECG signal 850 and their associated non-electrophysiological components developed from an accelerometer signal 835. Also illustrated is a detection window 870 that is used to evaluate correlation of the signals in accordance with an embodiment of the present invention. As is illustrated in FIG. 8, an S1 heart sound 832 and an S1 heart sound 834 are, in general, closely time correlated with a QRS complex 852 and a QRS complex 854, respectively. The S1 heart sound 832, an S2 heart sound 833, and the S1 heart sound 834 are illustrated as detected from an internally implanted accelerometer. The S1 heart sound may provide a close time correlation with cardiac signals but not with noise and artifact signals. As such, heart sounds may be used to discriminate a separated cardiac signal from other separated signals.

An ITCS device may be implemented to include signal processing circuitry and/or signal processing software as illustrated in FIGS. 1C and 1D. With continued reference to FIG. 8, signal processing may be used to correlate heart sounds, such as the S1 heart sound, with R-wave peaks or other QRS complex features to allow selection of the correct signal (i.e., the cardiac signal) after blind source separation or other separation technique has separated the ECG signal from various other signals.

In the approach illustrated in FIG. 8, the ITCS algorithm first identifies the S1 heart sound 832. An examination or detection window 870 is then defined to start at least before the peak of the S1 heart sound 832, illustrated as a preceding window start time 875. The algorithm then looks for time correlation between peak amplitudes on one of the separated channels with this examination window 870. The signal demonstrating highest correlation is designated to be the ECG signal. For example, the ECG signal 850 has an R-wave peak 856 falling within the examination window 870, and an R-wave peak 858 falling within an examination window 872. The R-wave peak 856 falling within the examination window 870 produces a large correlation value, indicating that the ECG signal 850 is time correlated to the S1 heart sound signal 832 within the examination window 870. Similarly, the R-wave peak 858 falling within the examination window 872 produces a large correlation value, indicating that the ECG signal 850 is time correlated to the S1 heart sound signal 834 within the examination window 872.

This approach to cardiac signal discrimination involves use of a non-electrophysiologic signal (e.g., the accelerometer signal 835) to select the ECG signal 850 from the various separated signals. The algorithm is robust, in that the heart sound information is not electrophysiological in nature, and therefore not susceptible to the same noise sources as the ECG signal 850.

Figure 9:
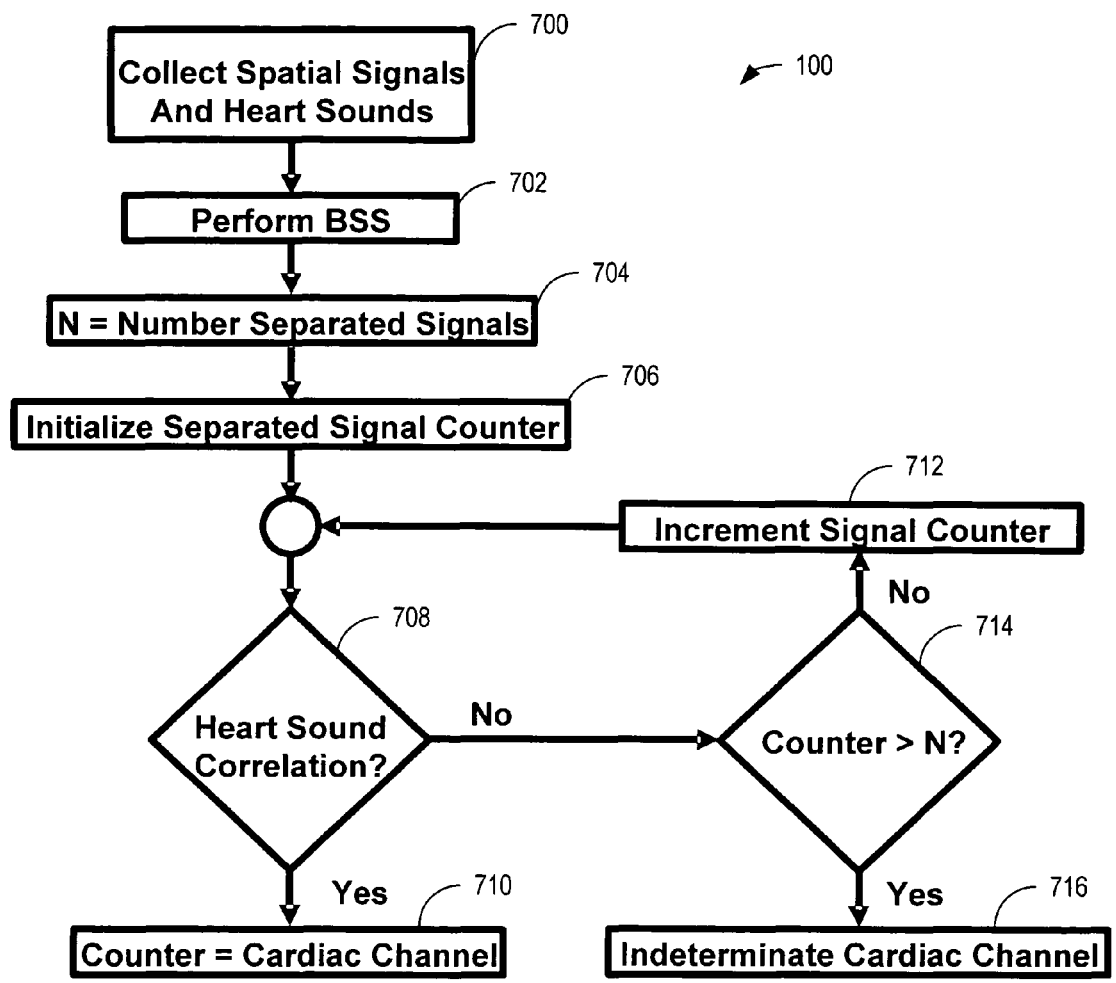
FIG. 9 is a flow chart of a method of signal separation in accordance with the present invention.

FIG. 9 illustrates the signal separation process 100 shown in FIG. 4, including various processes associated with a signal separation technique involving the use of heart sounds in accordance with the present invention. As shown in FIG. 9, signals are collected 700 from spatially diverse electrodes and one or more heart sound sensors (e.g., acoustic sensor(s)). A BSS routine, such as that discussed above, is performed 702 producing a number of separated signals 704. A counter 706 is set to a desired maximum number, N, of separated signals 704, and the separated signal counter 706 is initialized.

A heart sound/QRS complex correlation operation 708 is performed. If a detected heart sound is correlated with the QRS complex, then the sensed signal is deemed a cardiac signal 710. If the detected heart sound is not correlated with the QRS complex, the signal counter is compared 714 with the counter threshold, N. If the signal counter 706 is not greater than the counter maximum number, N, then the signal counter 706 is incremented at step 712 and the correlation operation 708 is repeated. If the signal counter 706 is greater than the counter maximum number, N, then the sensed signal is deemed indeterminate 716, and other hierarchical processes may be initiated.

An ITCS device may operate in a batch mode or adaptively, allowing for on-line or off-line implementation. To save power, the system may include the option for a hierarchical decision-making routine that uses algorithms known in the art for identifying presence of arrhythmias or noise in the collected signal and judiciously turning on the cardiac signal extraction routine of the present invention.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A signal separation method, comprising:
   detecting a composite electrical signal at a subcutaneous non-intrathoracic location, the composite electrical signal associated with a plurality of sources;
   receiving information associated with a non-electrophysiological cardiac source;
   separating a signal from the composite electrical signal using source separation; and
   verifying that the separated signal is a cardiac signal using the separated signal and the non-electrophysiological cardiac source information.

2. The method of claim 1, wherein verifying that the separated signal is the cardiac signal comprises providing a detection window defined by a start time and a stop time determined using the non-electrophysiological cardiac source information.

3. The method of claim 2, further comprising detecting a QRS complex within the detection window.

4. The method of claim 1, wherein the non-electrophysiological cardiac source information comprises acoustic emission information.

5. The method of claim 1, wherein the non-electrophysiological cardiac source information comprises a temporal location of a peak heart-sound.

6. The method of claim 5, wherein verifying that the separated signal is the cardiac signal comprises providing a detection window defined by a start time preceding the temporal location of a peak heart-sound.

7. The method of claim 1, wherein the non-electrophysiological cardiac source information comprises blood-flow information.

8. The method of claim 1, wherein the non-electrophysiological cardiac source information comprises pulse pressure information.

9. The method of claim 1, wherein the non-electrophysiological cardiac source information comprises pulse oximetry information.

10. The method of claim 1, wherein the non-electrophysiological cardiac source information comprises transthoracic impedance information.

11. The method of claim 1, wherein verifying that the separated signal is the cardiac signal comprises providing a detection window within which the cardiac signal is correlated to a signal associated with the non-electrophysiological cardiac source.

12. The method of claim 1, further comprising determining a time separation between a peak of the separated signal and a peak of a signal associated with the non-electrophysiological cardiac source.

13. The method of claim 12, wherein the time separation is used to identify a cardiac signal.

14. The method of claim 1, wherein the signal is separated from the composite electrical signal using blind source separation.

15. The method of claim 14, wherein the blind source separation comprises an independent component analysis performed on the composite electrical signal.

16. The method of claim 1, further comprising detecting a cardiac condition using the separated signal.

17. The method of claim 1, further comprising detecting a cardiac condition using the separated signal by performing a correlation between the separated signal and a signal associated with the non-electrophysiological cardiac source.

18. The method of claim 1, further comprising detecting a cardiac arrhythmia using the cardiac signal.

19. The method of claim 18, further comprising treating the cardiac arrhythmia.

20. An implantable device, comprising:
    means for subcutaneously detecting a composite electrical signal associated with a plurality of signal sources;
    means for subcutaneously detecting non-electrical cardiac activity;
    means for separating a signal from the composite electrical signal using source separation; and
    means for determining whether or not the separated signal is a cardiac electrical signal using the detected non-electrical cardiac activity.

21. The device of claim 20, wherein the determining means comprises means for performing a time correlation between the separated signal and a signal associated with the detected non-electrical cardiac activity.

22. The device of claim 20, wherein the determining means comprises means for evaluating the separated signal within a detection window.

23. The device of claim 22, further comprising means for determining a start time to initiate the detection window.

24. The device of claim 20, further comprising means for detecting an arrhythmia using the cardiac electrical signal.

25. The device of claim 24, further comprising means for treating the arrhythmia.

26. The device of claim 20, further comprising means for discriminating cardiac rhythms.

* * * * *